United States Patent
Sverrisson et al.

(10) Patent No.: US 10,179,055 B2
(45) Date of Patent: Jan. 15, 2019

(54) PUMP SYSTEM FOR USE WITH A PROSTHETIC DEVICE

(71) Applicant: Ossur Iceland ehf, Reykjavik (IS)

(72) Inventors: Atli Orn Sverrisson, Reykjavik (IS); Gudfinna Halldorsdottir, Reykjavik (IS)

(73) Assignee: OSSUR ICELAND EHF, Reykjavik (IS)

(*) Notice: Subject to any disclaimer, the term of this patent is extended or adjusted under 35 U.S.C. 154(b) by 0 days.

(21) Appl. No.: 15/163,117

(22) Filed: May 24, 2016

(65) Prior Publication Data

US 2016/0346100 A1   Dec. 1, 2016

Related U.S. Application Data

(60) Provisional application No. 62/168,088, filed on May 29, 2015.

(51) Int. Cl.
*A61F 2/68* (2006.01)
*A61F 2/70* (2006.01)
(Continued)

(52) U.S. Cl.
CPC .............. *A61F 2/80* (2013.01); *A61F 2/66* (2013.01); *A61F 2/68* (2013.01); *A61F 2/70* (2013.01); *A61F 2002/704* (2013.01); *A61F 2002/742* (2013.01); *A61F 2002/763* (2013.01); *A61F 2002/767* (2013.01); *A61F 2002/7625* (2013.01); *A61F 2002/7635* (2013.01); *A61F 2002/7655* (2013.01); *A61F 2002/7665* (2013.01); *A61F 2002/802* (2013.01); *F04B 45/04* (2013.01)

(58) Field of Classification Search
CPC ................................................ A61F 2002/742
See application file for complete search history.

(56) References Cited

U.S. PATENT DOCUMENTS 708,685 A    9/1902   White
980,457 A    1/1911   Toles
(Continued)

FOREIGN PATENT DOCUMENTS

AU    670631 B2    7/1996
BE    675 386 A    5/1966
(Continued)

OTHER PUBLICATIONS

International Search Report from corresponding PCT Application No. PCT/US20161033915, dated Jul. 29, 2016.
(Continued)

*Primary Examiner* — Jacqueline Woznicki
(74) *Attorney, Agent, or Firm* — Workman Nydegger

(57) ABSTRACT

A vacuum suspension system includes a prosthetic socket adapted to receive a residual limb. A pump system includes a pump mechanism in fluid communication with the prosthetic socket, and at least one sensor associated with the prosthetic socket and/or the pump mechanism. A control system is operably connected to the pump mechanism and the least one sensor. The control system is arranged to receive and process data from the at least one sensor and to actuate the pump mechanism based on the received data from the at least one sensor.

11 Claims, 4 Drawing Sheets

(51) Int. Cl.
  *A61F 2/80*   (2006.01)
  *A61F 2/66*   (2006.01)
  *A61F 2/74*   (2006.01)
  *A61F 2/76*   (2006.01)
  *F04B 45/04*   (2006.01)

(56) References Cited

U.S. PATENT DOCUMENTS

| | | |
|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,316,900 A | 5/1967 | Young |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,947,156 A * | 3/1976 | Becker ............ F04B 43/0054 417/413.1 |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,110,138 A | 8/2000 | Shirley |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,025,792 B2 | 4/2006 | Collier |
| 7,025,793 B2 | 4/2006 | Egilsson |
| 7,371,262 B2 | 5/2008 | Lecomte et al. |
| 7,427,297 B2 | 9/2008 | Patterson et al. |
| 7,448,407 B2 | 11/2008 | Alley et al. |

(56) References Cited

U.S. PATENT DOCUMENTS

| | | | |
|---|---|---|---|
| 7,468,079 B2 | 12/2008 | Collier | |
| 7,686,848 B2 | 3/2010 | Christensen | |
| 7,744,653 B2 | 6/2010 | Rush et al. | |
| 7,909,884 B2 | 3/2011 | Egilsson et al. | |
| 7,922,775 B2 | 4/2011 | Caspers | |
| 7,947,085 B2 | 5/2011 | Haines et al. | |
| 7,993,413 B2 | 8/2011 | Perkins et al. | |
| 8,007,543 B2 | 8/2011 | Martin | |
| 8,034,120 B2 | 10/2011 | Egilsson et al. | |
| 8,052,760 B2 | 11/2011 | Egilsson et al. | |
| 8,080,065 B2 | 12/2011 | Scussel et al. | |
| 8,097,043 B2 | 1/2012 | Egilsson | |
| 8,097,766 B2 | 1/2012 | Carlson et al. | |
| 8,114,167 B2 | 2/2012 | Caspers | |
| 8,298,294 B2 | 10/2012 | Kaltenborn et al. | |
| 8,317,876 B2 | 11/2012 | Mosler | |
| 8,343,233 B2 | 1/2013 | Perkins et al. | |
| 8,523,951 B2 | 9/2013 | Kania | |
| 8,894,719 B2 | 11/2014 | Egilsson et al. | |
| 8,956,422 B2 | 2/2015 | Halldorsson | |
| 8,961,618 B2 | 2/2015 | Lecomte et al. | |
| 9,044,348 B2 | 6/2015 | Halldorsson et al. | |
| 9,072,617 B2 | 7/2015 | Halldorsson et al. | |
| 9,198,780 B2 | 12/2015 | Jonsson et al. | |
| 9,259,332 B2 | 2/2016 | Danzig et al. | |
| 9,364,348 B2 | 6/2016 | Sandahl | |
| 9,486,335 B2 | 11/2016 | Halldorsson et al. | |
| 9,615,946 B2 | 4/2017 | Halldorsson et al. | |
| 9,757,256 B2 | 9/2017 | Sandahl | |
| 9,820,873 B2 | 11/2017 | Sandahl | |
| 9,889,025 B2 | 2/2018 | Jonsson et al. | |
| 9,943,421 B2 | 4/2018 | Sverrisson et al. | |
| 2001/0005798 A1 | 6/2001 | Caspers | |
| 2001/0016781 A1 | 8/2001 | Caspers | |
| 2002/0052663 A1* | 5/2002 | Herr | A61F 2/64 623/24 |
| 2002/0087215 A1 | 7/2002 | Caspers | |
| 2002/0091449 A1 | 7/2002 | Caspers et al. | |
| 2002/0103545 A1 | 8/2002 | Arbogast et al. | |
| 2002/0128580 A1 | 9/2002 | Carlson et al. | |
| 2003/0191539 A1 | 10/2003 | Caspers | |
| 2004/0024322 A1 | 2/2004 | Caspers | |
| 2004/0030411 A1* | 2/2004 | Caspers | A61F 2/5046 623/37 |
| 2004/0049290 A1* | 3/2004 | Bedard | A61F 2/644 623/24 |
| 2004/0064195 A1 | 4/2004 | Herr | |
| 2004/0122528 A1 | 6/2004 | Egilsson | |
| 2004/0163278 A1 | 8/2004 | Caspers et al. | |
| 2004/0181290 A1 | 9/2004 | Caspers | |
| 2004/0236434 A1 | 11/2004 | Carstens | |
| 2004/0260403 A1 | 12/2004 | Patterson et al. | |
| 2005/0131324 A1 | 6/2005 | Bledsoe | |
| 2005/0131549 A1 | 6/2005 | Caspers | |
| 2005/0143838 A1 | 6/2005 | Collier | |
| 2005/0240282 A1 | 10/2005 | Rush et al. | |
| 2005/0267603 A1 | 12/2005 | Lecomte et al. | |
| 2006/0074493 A1* | 4/2006 | Bisbee, III | A61F 2/5044 623/26 |
| 2006/0212130 A1 | 9/2006 | Collier | |
| 2006/0212131 A1 | 9/2006 | Curtis | |
| 2006/0224246 A1 | 10/2006 | Clausen et al. | |
| 2007/0005149 A1 | 1/2007 | Egilsson et al. | |
| 2007/0043316 A1 | 2/2007 | Carlson et al. | |
| 2007/0050044 A1* | 3/2007 | Haynes | A61F 2/68 623/24 |
| 2007/0055383 A1 | 3/2007 | King | |
| 2007/0112440 A1 | 5/2007 | Perkins et al. | |
| 2007/0196222 A1 | 8/2007 | Mosler et al. | |
| 2007/0204487 A1 | 9/2007 | Clough | |
| 2007/0213839 A1 | 9/2007 | Nachbar | |
| 2008/0086218 A1 | 4/2008 | Egilsson | |
| 2008/0147202 A1 | 6/2008 | Danzig et al. | |
| 2008/0147204 A1 | 6/2008 | Ezenwa | |
| 2008/0243266 A1 | 10/2008 | Haynes et al. | |
| 2008/0269911 A1 | 10/2008 | Street et al. | |
| 2008/0269912 A1 | 10/2008 | Gobbers et al. | |
| 2009/0036998 A1 | 2/2009 | Finlinson et al. | |
| 2009/0132056 A1 | 5/2009 | Kania | |
| 2009/0157196 A1 | 6/2009 | Danzig et al. | |
| 2009/0198346 A1 | 8/2009 | Perkins et al. | |
| 2009/0204229 A1 | 8/2009 | Mosler et al. | |
| 2009/0281637 A1* | 11/2009 | Martin | A61F 2/68 623/34 |
| 2010/0070051 A1 | 3/2010 | Carstens | |
| 2010/0087931 A1 | 4/2010 | Bogue | |
| 2010/0106260 A1 | 4/2010 | Phillips | |
| 2010/0262261 A1 | 10/2010 | Laghi | |
| 2010/0312359 A1 | 12/2010 | Caspers | |
| 2010/0312360 A1 | 12/2010 | Caspers | |
| 2010/0331749 A1 | 12/2010 | Powaser | |
| 2011/0035027 A1 | 2/2011 | McCarthy | |
| 2011/0046748 A1 | 2/2011 | Martin et al. | |
| 2011/0060421 A1 | 3/2011 | Martin et al. | |
| 2011/0071649 A1 | 3/2011 | McKinney | |
| 2011/0087142 A1 | 4/2011 | Ravikumar et al. | |
| 2011/0125291 A1 | 5/2011 | Tompkins et al. | |
| 2011/0130846 A1 | 6/2011 | Kampas et al. | |
| 2011/0184532 A1* | 7/2011 | Tompkins | A61F 2/68 623/34 |
| 2011/0202143 A1 | 8/2011 | Caspers | |
| 2011/0270413 A1* | 11/2011 | Haynes | A61F 2/68 623/34 |
| 2011/0295386 A1 | 12/2011 | Perkins et al. | |
| 2012/0000092 A1 | 1/2012 | Ingvarsson et al. | |
| 2012/0022667 A1* | 1/2012 | Accinni | A61B 5/4851 623/34 |
| 2012/0035520 A1 | 2/2012 | Ingimudarson et al. | |
| 2012/0123559 A1 | 5/2012 | Mosler et al. | |
| 2012/0173000 A1 | 7/2012 | Caspers | |
| 2012/0173001 A1 | 7/2012 | Caspers | |
| 2012/0191217 A1 | 7/2012 | Mackenzie | |
| 2013/0053982 A1 | 2/2013 | Halldorsson | |
| 2013/0096694 A1 | 4/2013 | Caldwell et al. | |
| 2013/0282142 A1 | 10/2013 | Perkins et al. | |
| 2013/0289741 A1 | 10/2013 | Halldorsson et al. | |
| 2014/0243997 A1 | 8/2014 | Clausen et al. | |
| 2014/0249648 A1 | 9/2014 | Sandahl | |
| 2016/0120665 A1 | 5/2016 | Muller | |
| 2016/0199202 A1 | 7/2016 | Jonasson et al. | |
| 2017/0056210 A1 | 3/2017 | Jonasson et al. | |
| 2017/0181871 A1 | 6/2017 | Halldorsson et al. | |
| 2018/0008436 A1 | 1/2018 | Sandahl | |
| 2018/0055659 A1 | 3/2018 | Sandahl et al. | |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685 861 C | 12/1939 |
| DE | 145 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |

(56) References Cited

FOREIGN PATENT DOCUMENTS

| | | |
|---|---|---|
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | H07-155343 A | 6/1995 |
| SE | 88-01686 L | 3/1989 |
| SU | 1667855 A1 | 8/1991 |
| SU | 1771722 A1 | 10/1992 |
| SU | 1812982 A3 | 4/1993 |
| SU | 1821177 A1 | 6/1993 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |
| WO | 01/54631 A1 | 8/2001 |
| WO | 01/70147 A2 | 9/2001 |
| WO | 02/26158 A2 | 4/2002 |
| WO | 02/065958 A2 | 8/2002 |
| WO | 02/067825 A2 | 9/2002 |
| WO | 02/080813 A2 | 10/2002 |
| WO | 03/077797 A2 | 9/2003 |
| WO | 03/099173 A1 | 12/2003 |
| WO | 03/099188 A1 | 12/2003 |
| WO | 2005/039444 A2 | 5/2005 |
| WO | 2005/105000 A1 | 11/2005 |
| WO | 2010/141960 A2 | 12/2010 |
| WO | 2011/035099 A1 | 3/2011 |
| WO | 2012010309 A1 | 1/2012 |
| WO | 2014126554 A1 | 8/2014 |
| WO | 2014194998 A1 | 12/2014 |
| WO | 2016112030 A1 | 7/2016 |

OTHER PUBLICATIONS

Brochure, "Sometimes Less is More, Harmony P3" Otto Bock, 12 pages. Available at, http://www.ottobock.com/cps/rde/xbcr/ob_es/646A303-EN-01-1001w.pdf, dated 2012.

Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.

Brochure,"Harmony Certification Course Manual," Original Harmony Pump, 42 pages. Availiable at, http://academy.ottobockus.com/videos/harmony/data/downloads/harmony%20course%20manual%202013.pdf. Dated 2013.

Brochure, Harmony P2 & HD, 2 pages. Available at http://www.ottobock.com/cps/rde/xchg/ob_us_en/hs.xsl/14904.html?id=4641. Dated 2012.

International Search Report from corresponding International PCT Application No. PCT/US2013/025849, dated Jun. 4, 2013.

International Search Report and Written Opinion from corresponding International PCT Application No. PCT/US2013/038668, dated Aug. 7, 2013.

Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.

International Search Report and Written Opinion from corresponding International PCT Application No. PCT/US2014/019218, dated May 9, 2014.

International Search Report from PCT Application No. PCT/US2016/012215, dated May 23, 2016.

International Search Report from PCT Application No. PCT/US2016/033707, dated Jul. 29, 2016.

International Search Report from PCT Application No. PCT/US2017/048354, dated Nov. 16, 2017.

International Search Report from PCT Application No. PCT/US2015/044434, dated Oct. 8, 2015.

International Search Report from PCT Application No. PCT/US2015/041089, dated Oct. 5.2015.

* cited by examiner

PUMP SYSTEM FOR USE WITH A PROSTHETIC DEVICE

TECHNICAL FIELD

The disclosure relates to the field of prosthetic devices, and more particularly to a pump system for regulating vacuum in a vacuum assisted suspension system.

BACKGROUND

An ongoing challenge in the development of prosthetic devices is the attachment of the prosthetic device to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb, or a liner donned on the limb, and a socket or receptacle coupled to the prosthetic limb. Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. Because the impact and displacement of the pump is not consistent and varies between users, the vacuum and thus attachment between residual limb and the socket can be unpredictable and/or inadequate, causing the user discomfort, grief and even injury. Electronic pumps are bulky and significantly contribute to the weight of the prosthetic limb, imposing a significant weight burden on the user when walking.

Both types of pumps typically require users to monitor and regulate vacuum levels in the socket with a simple dial pressure gauge, which can be time consuming and labor intensive. Moreover, dial pressure gauge readings are prone to user error and can be inconsistent from one user or dial pressure gauge to another. Further, dial pressure gauges are known to malfunction and typically have limited accuracy limits and measurement ranges. In addition, even with good readings, users must manually activate the pump to increase vacuum and introduce air into the socket from environment to decrease vacuum.

In view of the shortcomings of conventional systems and methods, there exists a substantial need for a system and method to monitor and regulate socket pressure that is more consistent, faster, less labor intensive, and provides higher accuracy.

SUMMARY

Embodiments of the disclosure provide more consistent, less labor intensive, and faster systems and methods to monitor and regulate socket pressure within a vacuum suspension system. According to an embodiment, a vacuum suspension system includes a prosthetic socket adapted for receiving a residual limb. A pump system includes a pump mechanism in fluid communication with the prosthetic socket, and at least one sensor associated with at least one of the prosthetic socket and the pump mechanism. A control system is operably connected to the pump mechanism and the at least one sensor. The control system is arranged to receive and process data from the at least one sensor and to actuate the pump mechanism based on the received data from the at least one sensor.

According to a variation, the at least one sensor can include a pressure sensor arranged to detect vacuum levels in the socket and/or pump mechanism. The control system can receive or obtain pressure information from the pressure sensor that can advantageously be used to regulate the vacuum inside the socket and/or monitor use of the vacuums suspension system, providing a more comfortable and/or safer fit. For instance, if the pressure information indicates that the vacuum within the socket is too low, the control system can direct the pump mechanism to increase negative pressure inside of the socket. If the pressure information indicates that the vacuum within the socket is too high, the control system can direct the pump mechanism to decrease negative pressure inside of the socket.

According to a variation, the at least one sensor can include a location sensor. The location sensor can detect the location and/or motion of one or more components of the vacuum suspension system. For instance, the location sensor can detect the location and/or motion of the pump mechanism, the residual limb, the socket, the prosthetic foot, a user, terrain, anatomical parts, and/or other suitable parts. The pump system or control system may obtain activity information from the data or feedback provided by the location sensor. The activity information can be associated with the socket, the pump mechanism, the prosthetic foot, the residual limb, and/or any other components or anatomical parts. Obtaining the activity information can include the control system or pump system reading the data, analyzing the data, transforming the data, and/or processing the data.

The activity information advantageously can be used to regulate the vacuum inside of the socket and/or monitor use of the system. For example, if the activity information indicates a user is running or in a period of activity, the control system can direct the pump mechanism to increase the negative pressure inside of the socket, creating a more secure fit between the socket and the residual limb. If the activity information indicates the user is sitting or in a period of inactivity, the control system can direct pump mechanism to decrease the negative pressure inside of the socket, providing a looser, more comfortable fit.

The activity information may also be used to obtain vacuum performance information about the effectiveness of the pump mechanism. For instance, change in pressure inside the socket can be compared to tibia angle during stance and swing phases to determine the effectiveness of the pump mechanism during gait. In other embodiments, change in pressure inside the socket can be compared to relative movement between the residual limb and the socket to determine the effectiveness of the pump mechanism when the residual limb changes in volume and/or during use. In other embodiments, change in pressure inside the socket can be compared to movement between the prosthetic foot, pump mechanism, and/or other component and the socket. Thus, by comparing pressure changes in the socket with a specific activity or condition, the effectiveness of the pump system can advantageously be monitored and/or accessed.

Another benefit is that the activity information can be used to compile medical information about a user and/or prosthetic products, thus improving the possibilities for better treatment, better prosthetic products, and/or better reimbursement procedures. For example, the activity information can be used to assess and record the fitness, health, and/or activity level of an amputee. If the activity information indicates the user is highly active, it can be used to fit the user to a higher performance or sport prosthetic foot and/or socket.

BRIEF DESCRIPTION OF THE DRAWINGS

These and other features, aspects, and advantages of the present disclosure will become better understood regarding the following description, appended claims, and accompanying drawings.

DETAILED DESCRIPTION OF THE DISCLOSURE

Figure 3:
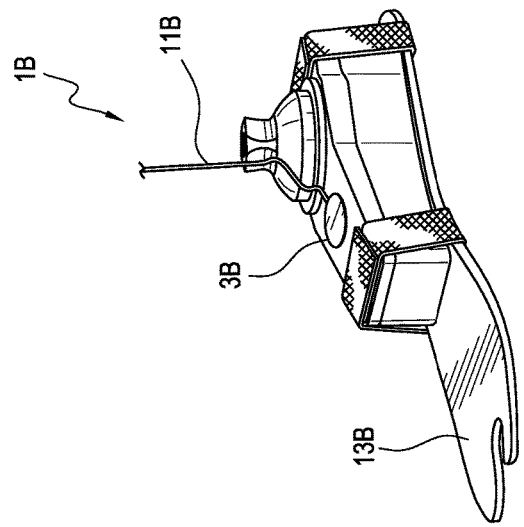
FIG. 3 shows a vacuum suspension system including a pump system according to another embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

The exemplary embodiments of a pump system can be used in various prosthetic systems, including, but not limited to, configurations of prosthetic sockets, prosthetic feet, vacuum suspension systems, prosthetic pylons, or any other suitable prosthetic system.

Figure 1:
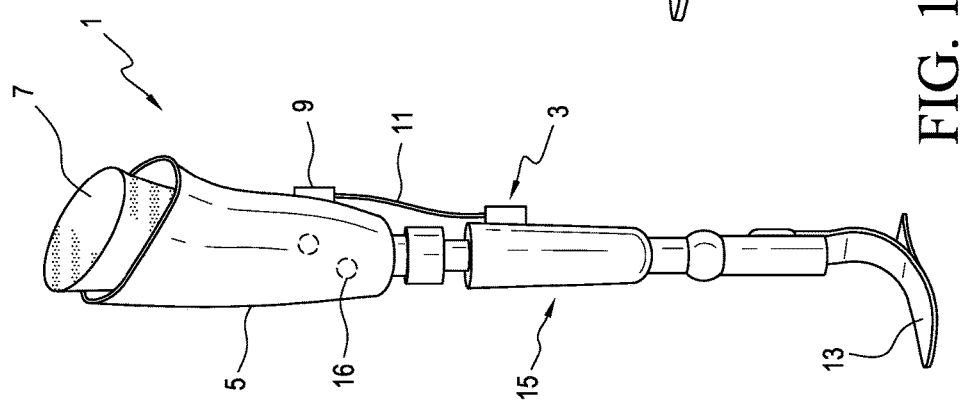
FIG. 1 shows a vacuum suspension system including a pump system according to an embodiment.

For instance, exemplary embodiments of a pump system can be implemented with a vacuum suspension system 1, as shown in FIG. 1. The exemplary vacuum suspension system 1 includes a socket 5, a liner 7 preferably including a seal component, a valve assembly 9, a tube 11 connecting the pump system 3 to the socket 5, and a prosthetic foot 13. The socket 5 defines an interior space, and interior wall delimiting the interior space. The vacuum suspension system 1 may also employ an adaptor system 15. Alternatively, the adaptor system 15 can include a shock and/or rotation module. The vacuum suspension system 1 provides improved proprioception and volume control since there is better attachment between the socket 5 and the residual limb.

In this embodiment, a pump system 3 is secured to the adaptor system 15. The pump system 3 is arranged to provide vacuum assisted suspension by generating a negative pressure (vacuum) inside the socket 5, resulting in a secure and reliable elevated vacuum suspension that provides an intimate suspension as the negative pressure inside of the socket 5 or socket pressure holds the liner and the residual limb firmly to the socket wall.

One or more sensors 16 may be associated with the pump system 3. The sensors 16 can be attached to or incorporated in the pump system 3. The sensors 16 can be separate or remote from the pump system 3. For instance, the sensors 16 can be attached to or incorporated in the socket 6 as shown. The sensors 16 may include pressure sensors detecting vacuum levels in the pump system 3 and/or socket 5, or the fit of the liner 7 and/or socket 5 over the residual limb. The sensors 16 may include temperature sensors. The sensors 16 may include humidity sensors. The sensors 16 may include sensors to measure limb movement within the liner 7 and/or the socket 5. The sensors 16 may include sensors to measure volume fluctuation of the residual limb throughout the day. The sensors 16 may include location sensors or sensors to determine how long the socket is worn or high periods of activity. The sensors 16 may include sensors for detecting heartrate and/or blood pressure of a user. It will be appreciated that other sensors may be used in the system 1 for different applications and for other diagnostic or physiological measurements.

Data or feedback from the sensors 16 can be used by the system 1 to obtain information related to the condition or state of the system 1 and/or user. For instance, data or feedback from the sensors 16 can be used by the pump system 3 to obtain pressure information, which, in turn, can be used to regulate the negative pressure inside the socket 5 and/or the pump system 3. In an embodiment, the pump system 3 can regulate the negative pressure inside the socket 5 by either increasing or decreasing the vacuum based on the pressure information. Decreasing vacuum can be done by introducing air from the environment into the socket 5. This can be done by the pump system 3 and/or the valve assembly 9. Increasing vacuum can be done by activating a pump mechanism of the pump system 3 to draw air out of the socket 5.

Regulating the vacuum level inside the socket based on the pressure information is advantageous because the vacuum level inside of the socket 5 must be sufficient to secure the residual limb within the socket 5 and prevent pistoning but if it is too high it may strangle the residual limb, causing discomfort and/or cutting off circulation of the residual limb. Too much vacuum can be especially dangerous for users with vascular disease and/or reduced sensation in the residual limb. By regulating the vacuum inside the socket 5, the pump system 3 thus provides a more secure, safe, and comfortable fit.

Optionally, the pressure information can be communicated to an end user, such as, but not limited to, a user (e.g., amputee), a computer device, a CPO (Certified Prosthetist/Orthotist), and/or a rehabilitation doctor by the pump system 3. For instance, the pump system 3 can communicate to a CPO almost immediately if the socket 5 is or is not holding proper vacuum as opposed to requiring the end user to manually and repeatedly check vacuum levels in the socket using a dial pressure gauge as in the prior art. This approach assists in maximizing the comfort and safe use of the prosthesis. It also advantageously is faster, more accurate, and more consistent than conventional systems and methods.

Data or feedback from the sensors 16 can be used by the pump system 3 to obtain activity information associated with the user and/or system. The activity information associated with the user can include heartrate, blood pressure, breathing rate, and/or other types of information. Such information can be used to regulate the vacuum inside of the socket 5 and/or the system 1. For example, if the activity information indicates a user is running or descending stairs, the pump system 3 can direct the pump mechanism described below to increase the negative pressure inside of the socket 5, creating a more secure fit between the socket 5 and the user's residual limb. If the activity information indicates the user is sitting, the pump system 3 can direct pump mechanism to decrease the negative pressure inside of the socket 5, providing a looser, more comfortable fit.

The activity information can also be used to obtain vacuum performance information about the effectiveness of the pump mechanism. For instance, change in pressure inside the socket 5 can be compared to tibia angle during stance and swing phases to determine the effectiveness of the pump mechanism during gait. In other embodiments, change in pressure inside the socket 5 can be compared to relative movement between the residual limb and the socket 5 to determine the effectiveness of the pump mechanism when the residual limb changes in volume and/or during use.

In other embodiments, change in pressure inside the socket 5 can be compared to movement between the prosthetic foot, pump mechanism, and/or other component and the socket. Thus, by comparing pressure changes in the socket 5 with a specific activity or condition, the effectiveness of the pump system 3 can advantageously be monitored and/or accessed.

Another benefit is that the activity information can be used to compile medical information about the user and/or prosthetic products, thus improving the possibilities for better treatment, better prosthetic products, and/or better reimbursement procedures. For example, the activity information can be used to assess and record the fitness, health, and/or activity level of a user or amputee. In an embodiment, the sensors 16 can sense heartrate or blood pressure of the user. Data including information related to the heartrate or blood pressure can then be communicated from the sensors 16 or pump system 3 to the cloud, a computer device, or a computer system described below so that a third party can access and use the data to monitor the overall health and/or stress of the user.

Figure 2:
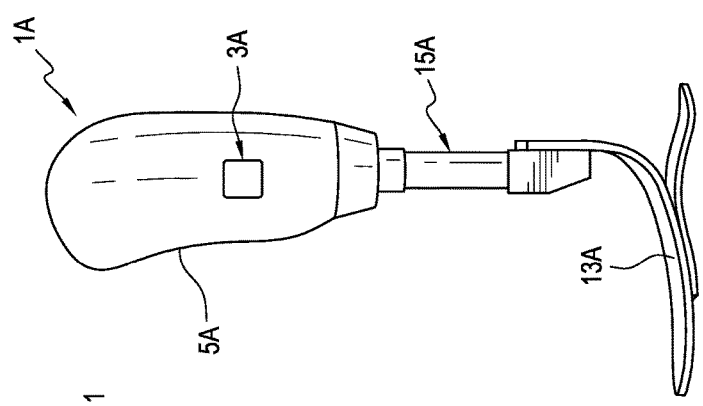
FIG. 2 shows a vacuum suspension system including a pump system according to another embodiment.

Further, exemplary embodiments of a pump system can be implemented directly with a socket, as shown in FIG. 2. For instance, a vacuum suspension system 1A can include socket 5A, a prosthetic foot 13A, and an adaptor system 15A connecting the socket 5A to the prosthetic foot 13A. A pump system 3A can be secured directly to a sidewall of the socket 5A. Because the pump system 3A is located at the socket 5A, there is no need to move fluid drawn into the pump system 3A from the socket 5A down to another prosthetic component such as the foot 13A. This advantageously reduces the time to produce an elevated vacuum in the socket 5A. Further, it can eliminate the need for a long tube extending between the pump mechanism and another component, reducing the likelihood of leaks and increasing the accuracy of the pump system 3A.

FIG. 3 shows yet another embodiment of a pump system implemented with a prosthetic foot. As seen, a vacuum suspension system 1B can include a prosthetic foot 13B and a pump system 3B can be secured directly to the foot 13B. A tube 11B can fluidly connect the pump system 3B to a prosthetic socket. The pump system 3B can be secured to the foot 13B such that there is a reduced likelihood of the pump system 3B undesirably affecting the functionality of the foot 13B, providing a more natural gait. The pump system 3B can be located on a proximal surface of the foot 13B, providing a sleek and low-profile design.

Figure 5:
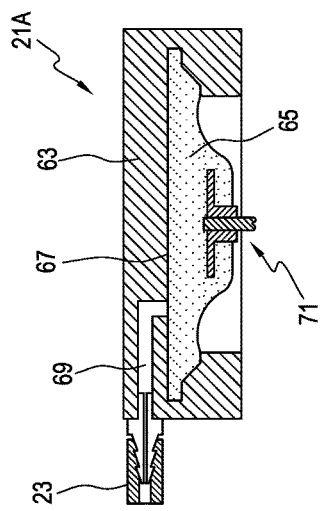
FIG. 5 shows a cross section view of the pump mechanism in FIG. 4 according to an embodiment.
Figure 6:
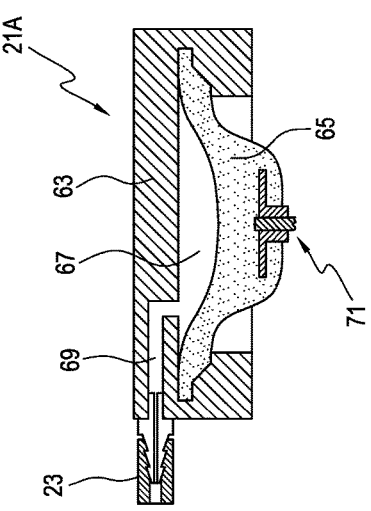
FIG. 6 shows another cross section view of the pump mechanism in FIG. 4 according to an embodiment.
Figure 4:
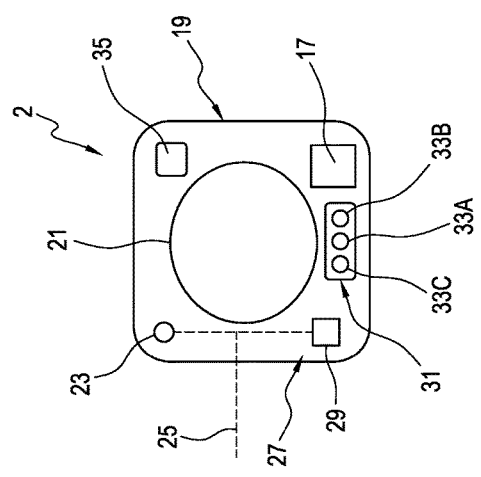
FIG. 4 shows a pump system according to an embodiment.

FIGS. 4-6 illustrate a pump system according to an embodiment of the disclosure. As seen, a pump system 2 can include a housing 19 containing a pump mechanism 21 arranged to be in fluid communication with the cavity of the socket 5. The pump mechanism 21 can be operable to draw out of the socket 5 and/or introduce air into the socket 5.

At least one valve assembly 23 is in fluid communication with the pump mechanism 21 that can control the flow of fluid (e.g., air) into and/or out of the pump mechanism 21. For instance, the at least one valve assembly 23 can include an inlet valve that only allows fluid to enter the pump mechanism 21, which can be connected to a tube system 25 as shown. The pump mechanism 21 can draw fluid (e.g., air) out from the socket 5 via the tube system 25 and the inlet valve.

The at least one valve assembly 23 can include an outlet valve that only allows fluid to be expelled out of the pump mechanism 21, preferably to atmosphere. In some embodiments, the inlet and outlet valves can be integrated in the same valve assembly.

Similar to the previous embodiments, one or more sensors 27 can be associated with the pump system 2. The sensors 27 can be separate or remote from the pump system 2. The sensors 27 can be attached to or incorporated in the pump system 2. For instance, the sensors 27 can include a pressure sensor 29 attached to the housing 19 for measuring pressure levels in the pump system 2 and/or the fit of the liner 7 and/or socket 5 over the residual limb. In an embodiment, the pressure sensor 29 can measure pressure levels inside the socket 5 during use. The pressure sensor 29 can be in fluid communication with the pump mechanism 21, the socket 5, and/or the tube system 25.

The pump system 2 can obtain pressure information associated with the socket 5 and/or pump system 2 from the pressure data or feedback provided by the pressure sensor 29. Obtaining the pressure information can include reading the data, analyzing the data, transforming the data, and/or processing the data. The pressure information obtained by the pump system 2 advantageously can be used to regulate the vacuum inside of the socket 5 and/or monitor use of the system 1, providing a more comfortable and/or safer fit. For instance, if the pressure information indicates that the pressure within the socket 5 is too high, the pump system 2 can direct to the pump mechanism 21 to create negative pressure inside of the socket 5.

The sensors 27 can include a location sensor 17. The location sensor 17 is shown positioned on and/or inside of the housing 19 but can be positioned in any suitable location. The location sensor 17 can detect the location and/or motion of one or more components of the vacuum suspension system 1. For instance, the location sensor 17 can detect the location and/or motion of the pump mechanism 21, the residual limb, the socket, the prosthetic foot, the user, terrain, anatomical parts, and/or other suitable parts.

The pump system 2 is arranged to obtain activity information from the data or feedback provided by the location sensor 17. The activity information can be associated with one or more components of the system 1 such as, but not limited to, the socket 5, the pump mechanism 21, the prosthetic foot, the residual limb, and/or any other components or anatomical parts. Obtaining the activity information can include the pump system 2 reading the data, analyzing the data, transforming the data, and/or processing the data.

The activity information advantageously can be used to regulate the vacuum inside of the socket 5 and/or monitor use of the system 1. For example, if the activity information indicates a user is running, the pump system 2 can direct the pump mechanism to increase the negative pressure inside of the socket 5, creating a more secure fit between the socket 5 and the residual limb. If the activity information indicates the user is sitting, the pump system 2 can direct pump mechanism 21 to decrease the negative pressure inside of the socket 5, providing a looser, more comfortable fit.

The activity information can also be used to obtain vacuum performance information about the effectiveness of the pump mechanism. For instance, change in pressure inside the socket 5 can be compared to tibia angle during stance and swing phases to determine the effectiveness of the pump mechanism during gait. In other embodiments, change in pressure inside the socket 5 can be compared to relative movement between the residual limb and the socket 5 to determine the effectiveness of the pump mechanism when the residual limb changes in volume and/or during use. In other embodiments, change in pressure inside the socket 5 can be compared to movement between the prosthetic foot, pump mechanism, and/or other component and the socket. Thus, by comparing pressure changes in the socket 5 with a specific activity or condition, the effectiveness of the pump system can advantageously be monitored and/or accessed.

Another benefit is that the activity information can be used to compile medical information about a user and/or prosthetic products, thus improving the possibilities for better treatment, better prosthetic products, and/or better reimbursement procedures. For example, the activity information can be used to assess and record the fitness, health, and/or activity level of an amputee. If the activity information indicates the user is highly active, it can be used to fit the user to a higher performance or sport prosthetic foot and/or socket.

The location sensor 17 can include an inertial measurement unit (IMU) having at least one accelerometer, gyroscope, and/or magnetometer. The location sensor 17 can include a strain gauge, a force sensitive resistor, and/or a distance sensor. The location sensor 17 can be a light sensor, a force sensor, a motion sensor, a position sensor, a time detector (e.g., timer, clocks), temperature sensor, and/or any other suitable type of sensing device.

It will be appreciated that any of the sensing capabilities disclosed herein can be present in a single sensor or an array of sensors. Further, sensing capabilities are not limited to a particular number or type of sensors. Moreover, the sensors can be located in any suitable portion of the vacuum suspension system 1. For instance, at least one of the sensors can be located in the tubing system, the socket, or the liner.

The pump system 2 can include a feedback system 31 for communicating at least a portion of the information obtained by the pump system 2 to an end user. In an embodiment, the feedback system 31 can communicate to the end user when the pressure information indicates the pressure inside the socket 5 is above a value limit. For instance, the feedback system 31 can include a set of three light emitting diodes 33 and a vibrator 35. If the pressure information obtained by the pump system 2 indicates the pressure in the socket 5 is good, the feedback system 31 can illuminate a green LED 33A, communicating to the end user that the vacuum is good. If the pressure information indicates the pressure in the socket 5 is poor, the feedback system 31 can illuminate a yellow LED 33B and/or vibrate the vibrator 35, alerting the end user that the vacuum is poor.

If the pressure information obtained by the pump system 2 indicates the pressure in the socket 5 is too high, the feedback system 31 can illuminate a red LED 33C, alerting the end user that the vacuum is too much. The pump system 2 can thus communicate to the end user almost immediately if the socket 5 is or is not holding proper vacuum as opposed to requiring a user to manually and repeatedly check vacuum levels in the socket, improving user comfort and safe use. It also has the effect of reducing the likelihood of user error because the user is not required to a read a dial pressure gauge. It is also advantageously faster, more accurate, and more consistent than conventional systems and methods.

In other embodiments, the feedback system 31 can include an audible feedback alarm, a feedback alarm that shocks a user, and/or any suitable type of interface device. In yet other embodiments, one or more portions of the feedback system 31 can be integrated with a mobile device described below.

FIGS. 5 and 6 illustrate a pump mechanism 21A according to an embodiment. The pump mechanism 21A can include a pump housing 63, a membrane 65, and an actuator 71. The pump mechanism 21A relies upon deformation of the membrane 65 to move between an original configuration in which the volume of a fluid chamber 67 defined between the membrane 65 and the pump housing 63 is zero or near-zero, and an expanded configuration in which the volume of the fluid chamber 67 is increased. The pump housing 63 is arranged to surround the outer radial edge of the membrane 65 and creates a seal with the membrane 65. The pump housing 63 can define at least one opening that extends into the pump housing 63 to form at least one internal passageway 69 to provide fluid communication between the fluid chamber 67 and a socket. In an embodiment, the internal passageway 69 can be in fluid communication with the fluid chamber 67 and at least one valve 23 of the pump system 2. Optionally, the at least one valve 23 can be attached directly to the pump housing 63 as seen in FIGS. 5 and 6. In other embodiments, the at least one valve 23 can be separate from the pump housing 63.

The actuator 71 can move the pump mechanism 21A between the original and expanded configurations. For instance, rotation of the actuator 71 in a first direction can move the pump mechanism 21A toward the expanded configuration and rotation of the actuator 71 in a second direction, opposite the first, can move the pump mechanism 21A toward the closed configuration. The actuator 71 can be driven by any suitable drive module.

Other examples of the pump mechanism 21 are described in U.S. Pat. Nos. 9,044,348; 9,072,617; and 9,198,780 and U.S. patent application Ser. No. 14/988,503, and commercially available as the Unity Vacuum System by Ossur hf. This disclosure is incorporated by reference and belongs to the assignee of this disclosure. In other embodiments, the pump mechanism 21 can be an electric vacuum generator, a membrane-type pump, a bladder-type pump, a peristaltic pump, a piston-type pump, or any other suitable pump mechanism.

Figure 7:
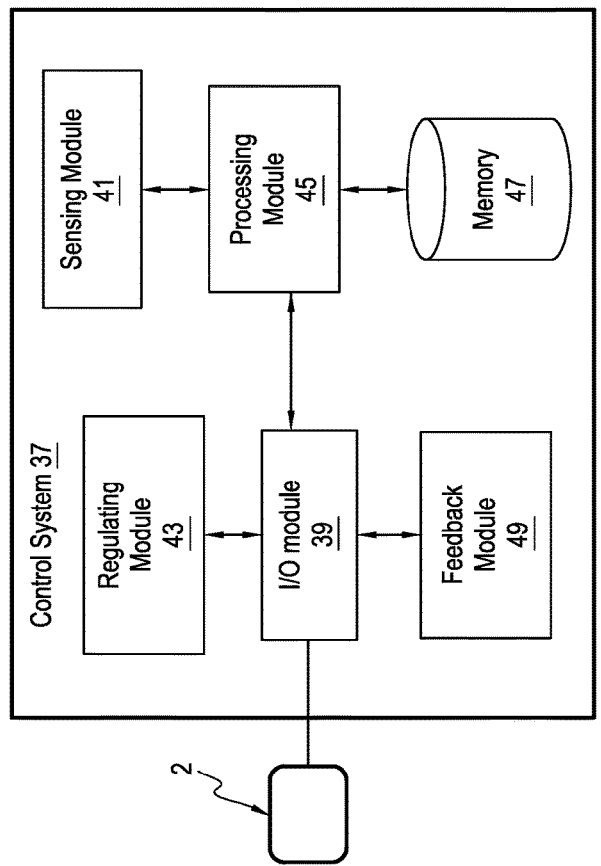
FIG. 7 shows an architectural schematic diagram of the pump system shown in FIG. 4.

As seen in FIG. 7, a control system 37 can be associated with the pump system 2. The control system 37 can be operable to control operation of one or more of the foregoing system components (e.g., pump mechanism 21, valve assembly 23, sensors 27, feedback system 31). The control system 37 can be internal to or external to the pump system 3. The control system 37 may be programmable for regulating pressure inside the socket 5 and/or monitoring activity of the user and/or vacuum suspension system 1.

The control system 37 can include an input/output (I/O) module 39. The I/O module 39 can communicate with the pump system 2, the valve assembly 9, an end user, other modules of the control system 37, and/or other devices. A processing module 45 can execute computer executable instructions and/or process data. The processing module 45 may be operably coupled to a memory 47. The memory 47 can store an application including computer executable instructions, measurement data, and/or operational data constituting a program to perform certain acts (e.g., a part program, a software control program, etc.). For example, the processing module 45 may be operably coupled to the memory 47 storing an application including computer executable instructions and data constituting a customized program to regulate vacuum in the socket 5.

The memory 47 may be embodied as a computer readable medium, such as a random access memory ("RAM"), a hard disk drive, or a static storage medium such as a compact disk, DVD, or the like. The memory 47 may include the cloud or a network described below. The memory 47 may further store information and/or data obtained by the pump system 2.

Through the I/O module 39, a sensing module 41 can direct one or more of the sensors 27 to detect pressure levels in the socket 5 and/or the vacuum suspension system 1. According to a variation, the sensing module 41 can direct one or more of the sensors 27 to detect movement/location of different components of the vacuum suspension system 1. In other embodiments, the sensing module 41 can direct one or more of the sensors 27 to detect heartrate and/or blood pressure of the user.

Upon receiving data from the sensors 27, a regulating module 43 can direct the pump mechanism 21 to vary the vacuum in the socket 5 and/or vacuum suspension system 1. The regulating module 43 and/or the processing module 45 can obtain pressure information from the data collected by the sensors 27. Based on the pressure information, the regulating module 43 can direct the pump mechanism 21 to increase and/or decrease the vacuum in the socket 5. For instance, if the pressure information indicates that the vacuum in the socket 5 is too low, the regulating module 43 can direct the pump mechanism 21 to increase the vacuum. If the pressure information indicates the vacuum in the socket 5 is too high, the regulating module 43 can direct the valve assembly 9 to decrease the vacuum in the socket 5 by introducing air into the socket 5. As noted above, obtaining the pressure information can include reading the data, analyzing the data, transforming the data, and/or processing the data.

A feedback module 49 can direct the feedback system 31 to communicate information obtained by the pump system 2 to an end user (e.g., user or CPO) via the I/O module 39. For example, if the pressure information indicates that the vacuum in the socket 5 is too low, the feedback module 49 can direct the yellow LED 33B to illuminate and/or the vibrator 35 to vibrate, alerting the end user of a potential dangerous fit between the socket 5 and the residual limb. In other embodiments, the control system 37 can include a monitoring module for obtaining the pressure information which can then be communicated to a user, CPO, and/or other intended party via the I/O module 39 for monitoring purposes. For instance, the regulating module 43 and/or the feedback module 49 may be omitted and the control system 37 may include the monitoring module. In other embodiments, the monitoring module may be integrated with the regulating module.

Figure 8:
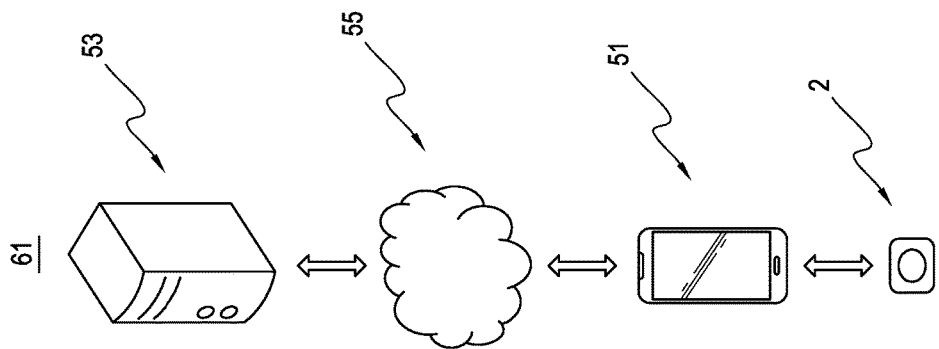
FIG. 8 shows another architectural schematic diagram of the pump system shown in FIG. 4.

The control system 37 can be internal to or external to the pump system 3. For instance, the control system 37 can comprise or can be operably coupled to a system 61 having a computer device 51 as seen in FIG. 8.

The computer device 51 can display information to an end user and receive user input, respectively. As seen, the computer device 51 preferably is a mobile device. A mobile device is defined as a processing device routinely carried by a user. It typically has a display screen with touch input and/or a keyboard, and its own power source. As such, the computer device 51 can provide a user the freedom to use it almost anywhere.

The computer device 51 can be a hand-held device. The computer device 51 can be a tablet computer, a smartphone, a laptop, a mobile telephone, a PDA, or other appropriate device. It will be appreciated that any of the methods and systems described herein may be adapted to couple the pump system 2 to a computer device 51 such as a desktop computer or the like in place of the mobile device.

The computer device 51 is communicatively coupled to the pump system 3. The computer device 51 can be communicatively coupled to a server or computer system 53 over a network 55, such as for example, a Local Area Network ("LAN"), a Wide Area Network ("WAN"), and even the internet. The computer system 53 can be located remotely from the computer device 51. The computer system 53 can be used for controlling and/or monitoring the computer device 51 and/or the pump system 2. The computer system 53 can be used for exchanging information/files with the computer device 51 and/or pump system 2. For instance, the pump system 2 can send one or more files including pressure information and activity information to the computer device 51.

The exact division of labor between the computer device 51, the pump system 2, and the computer system 53 may vary. For instance, the computer device 51 can perform nearly all operations and the pump system 2 merely carries out instructions that are received from the computer device 51. At the other end of the spectrum, the computer device 51 receives and stores data/files from the pump system 2, and the pump system 2 performs all other operations. Any division of labor between the pump system 2, the computer device 51, and the computer system 53 is also within the scope of the present disclosure.

A vacuum regulating routine or application of the pump system 2 will now be described according to an embodiment. First, a vacuum regulating routine or application can be initiated in which the pump system 2 directs the sensors 27 to measure the vacuum in the socket 5 (shown in FIG. 1). This can include receiving user input specifying the initiation of the routine by the pump system 2 and/or other feedback or input. Upon initiation of the routine, the sensing module 41 can output one or more sensing instructions via the I/O module 39 to the pressure sensor 29 without human intervention (e.g., without input from an operator). Automatically and without human intervention, the pressure sensor 29 can measure the pressure level within the socket 5 in accordance with the measurement instructions. The pressure data can be sent to one or more of the modules and/or stored in the memory 47 via the I/O module 39.

Upon receiving the pressure data, the regulating module 43 can obtain pressure information from the pressure data. Obtaining the pressure information can include reading the data, analyzing the data, transforming the data, and/or processing the data. For example, the regulating module 43 and/or the processing module 45 can compare the pressure data to a value limit stored in the memory to obtain the pressure information.

Based on the pressure information, the regulating module 43 can output one or more pumping instructions via the I/O module 39 to the pump mechanism 21. If the pressure information indicates the pressure in the socket 5 is above the value limit, the pumping instructions can direct the pump mechanism 21 to increase the vacuum in the socket 5. If the pressure information indicates the pressure in the socket 5 is below the value limit, the pump instructions can direct the pump mechanism 21 and/or the valve assembly 9 (shown in FIG. 1) to decrease the vacuum in the socket 5. The pump mechanism and/or valve assembly 9 can then increase and/or decrease the pressure in the socket 5 based on the pumping instructions.

The value limit can be a singular value, a set of values, or a range of values. The value limit can be a relative or absolute pressure level. The value limit can be a range of target pressure levels. The value limit can be selected based on user activity criteria and/or any other suitable criteria. In an embodiment, the value limit can be set using an application on the computer device 51 or hand-held device.

A feedback routine can include the feedback module 49 outputting one or more feedback instructions via the I/O module 39 to the feedback system 31 based upon the pressure information. For instance, if the pressure information indicates that the vacuum in the socket 5 is good, the feedback instructions can direct the green LED 33A to illuminate, confirming a secure and comfortable fit between the socket 5 and the residual limb. If the pressure information indicates that the vacuum is too high, the feedback instructions can direct the red LED 33C to illuminate, alerting the end user of a fit between the socket 5 and the residual that may be too tight. If the pressure information indicates that the vacuum is poor, the feedback instructions can direct the yellow LED 33B to illuminate, alerting the end user that the socket 5 may detach from the residual limb. The feedback instructions can also direct the vibrator 35 to vibrate if the pressure information indicates the vacuum is poor and/or too high, providing the user feedback regarding whether there is a proper fit between the residual limb and the socket 5.

In some embodiments, the feedback instructions can instruct the I/O module 39 to send the pressure information to the network 55 and/or computer system 53 through the computer device 51 for additional analysis and/or storage.

An activity routine or application according to an embodiment will now be described. First, an activity routine can be initiated in which the pump system 2 directs the sensors 27 to measure the activity of a user. This can include receiving user input specifying the initiation of the routine by the pump system 2 and/or feedback from one or more of the sensors 27. Upon initiation of the routine, the sensing module 41 can output one or more sensing instructions via the I/O module 39 to the location sensor 17.

The location sensor 17 can measure the activity of the user in accordance with the sensing instructions. For instance, the location sensor 17 can measure movement of the pump mechanism 21 based on the sensing instructions. The location sensor 17 can measure movement of the prosthetic foot 13 based on the sensing instructions. The location sensor 17 can measure the load and/or moment on the prosthetic foot 13 based on the sensing instructions. The location sensor 17 can measure movement of the residual limb relative to the socket 5 based on the sensing instructions. The location sensor 17 can measure stride, stride count, and/or stride count over time based on the sensing instructions. The location sensor 17 can measure speed and/or cadence of the user's gait based on the sensing instructions. The location sensor 17 can measure terrain based on the sensing instructions such as, for example, but not limited to, grade, ground hardness, and/or stairs climbing up and down. The location sensor 17 can measure stride time, stance time, swing time, active time on the prosthetic socket 5, and/or inactive time on the prosthetic socket 5 based on the sensing instructions. The location sensor 17 can measure tibia angle during stance and/or swing phase based on the sensing instructions. In other embodiments, the location sensor 17 and/or another one of the sensors 27 can measure the user's heart rate, blood pressure, and/or breathing rate.

The data collected by the location sensor 17 can be sent to one or more modules and/or stored in the memory 47 via the I/O module 39. For example, the processing module 45 and/or the regulating module 43 can obtain activity information from the data collected by the location sensor 17, which, in turn, can be used to compile medical information about the user, information about the vacuum suspension system, the pump system, and/or the prosthetic foot. The activity information can be associated with one or more components of the system 1.

In some embodiments, the activity information can be used by the regulating module 43 and/or other modules to regulate the vacuum in the socket. For example, if the activity information indicates the user is in a period of activity or exercising (e.g., hiking, running, jogging, walking, jumping, climbing, or the like) the regulating module 43 can send pumping instructions to the pump mechanism 21 directing it to increase the vacuum in the socket 5. If the activity information indicates the user is in a period of inactivity, the regulating module 43 can send pumping instructions to the pump mechanism 21 directing it to decrease the vacuum in the socket 5. By way of example, if the activity information indicates the user is skiing and the vacuum inside the socket 5 is not sufficient to maintain the connection between the socket 5 and the residual limb during skiing, the feedback module 49 can send feedback instructions to the feedback system 31 to warn the user of insufficient vacuum. Using the activity information to regulate the vacuum in the socket increases user comfort and safe use of the prosthesis.

It also allows for the gathering of medical information about the user and/or prosthetic foot, thus improving the possibilities for better treatment, better prosthetic products, and/or better reimbursement procedures. For instance, the activity information can provide information about the performance of the prosthetic foot during walking or stretching. In other embodiments, the activity information can provide information about the user's health during specific activities or in general. For instance, the activity information can provide information to a third party medical professional that the user is having a heart attack or stroke.

The activity information can also be used to evaluate performance of the pump mechanism 21. For instance, a vacuum performance routine or application according to an embodiment will now be described. The vacuum performance routine can be similar to the routines previously described except that it obtains vacuum performance information from the pressure and activity information.

In an embodiment, pressure information can be compared to activity information during a specific activity to evaluate the activity effectiveness of the pump system 2 and/or pump mechanism 21. By way of example, change in pressure inside the socket 5 can be compared to tibia angle during stance and swing phases to determine the effectiveness of the pump mechanism during gait. In other embodiments, change in pressure inside the socket 5 can be compared to relative movement between the residual limb and the socket 5 to determine the effectiveness of the pump mechanism when the residual limb changes volume and/or during use of the vacuum suspension system. In other embodiments, change in pressure inside the socket 5 can be compared to movement between the prosthetic foot, pump mechanism, and/or other component and the socket.

Thus, by comparing pressure changes in the socket 5 with a specific activity or condition, the effectiveness of the pump system 2 can advantageously be monitored and/or accessed. Further, the pump system 2 can be controlled based on different needs and/or activities of a user, providing versatility and useful information.

In addition to the foregoing, one will appreciate that embodiments of the present disclosure can also be described in terms of flowcharts including one or more steps for accomplishing a particular result. For instance, the steps of FIG. 9 and the corresponding text describe steps in a method for regulating vacuum in a socket with a pump system. The steps in FIG. 9 are described below with respect to the components and modules in FIGS. 1-8.

Figure 9:
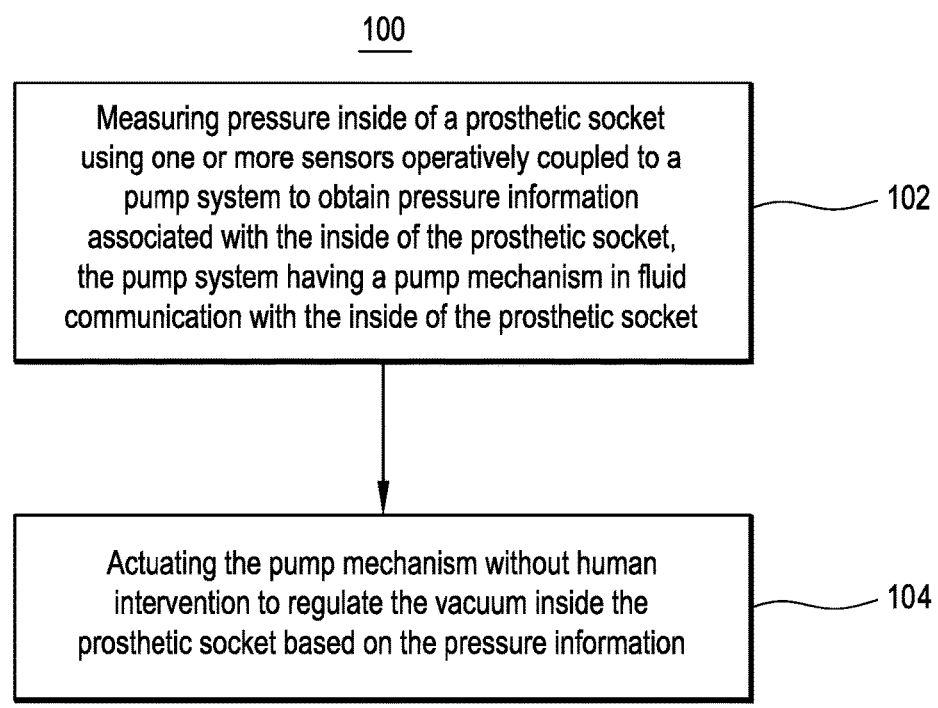
FIG. 9 shows an overview of the steps in an embodiment of the vacuum monitoring method.

For instance, FIG. 9 illustrates a method 100 in accordance with the present disclosure for regulating vacuum in a socket with a pump system includes a step 102 measuring pressure inside of a prosthetic socket using one or more sensors operatively coupled to a pump system to obtain pressure information associated with the inside of the socket. Step 102 can include the control system obtaining the pressure information from the data provided by the pressure sensor. For instance, FIG. 7 and the accompanying description depict and describe the regulating module 43 comparing data from the pressure sensor to a value limit to obtain pressure information and outputting pumping instructions to the pump mechanism based on the pressure information.

Additionally, FIG. 9 shows that the method 100 can include a step 104 of actuating the pump mechanism without human intervention to regulate vacuum inside the prosthetic socket based on the pressure information. Step 104 can include the control system outputting pumping instructions directing the pump mechanism to increase or decrease the vacuum in the socket based on the pressure information. For instance, FIG. 7 and the accompanying description depict and describe the regulating module transmitting pumping instructions to the pump mechanism and/or valve assembly to increase or decrease the vacuum in the socket based on the pressure information. The pump mechanism and/or valve assembly can then vary the vacuum inside of the prosthetic socket based on the pumping instructions.

Accordingly, FIGS. 1-9 provide a number of components, schematics and mechanisms for regulating a vacuum in a prosthetic socket with a pump system based on feedback from one or more sensors. This has the effect of providing a more secure, safe, and comfortable fit between the socket and the residual limb. This also advantageously is faster, more accurate, and more consistent than conventional systems and methods.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, or a combination, all of which can be behaviorally equivalent. Modules may be implemented using computer hardware in combination with software routine(s) written in a computer language. It may be possible to implement modules using physical hardware that incorporates discrete or programmable analog and/or digital hardware. Examples of programmable hardware include computers, microcontrollers, microprocessors, application-specific integrated circuits, field programmable gate arrays, and complex programmable logic devices.

As noted above, the pressure regulating, activity monitoring, and/or vacuum performance routines or applications may be software embodied on a computer readable medium which when executed by a processor component of a computer device performs a sequence of steps. The application may be a mobile application or application software configured to run on smartphones, tablets computers, and/or other mobile devices.

Moreover, embodiments of the present disclosure may comprise or utilize a special-purpose or general-purpose computer system that includes computer hardware, such as, for example, one or more processors and system memory, as discussed in greater detail below. Embodiments within the scope of the present disclosure also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the disclosure can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the disclosure.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the disclosure may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud computing model can be composed of various characteristics, such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth.

Some embodiments, such as a cloud computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A vacuum suspension system comprising:
   a prosthetic socket adapted for receiving a residual limb;
   a pump system including a pump mechanism in fluid communication with the prosthetic socket, and a plurality of sensors associated with at least one of the prosthetic socket and the pump mechanism, the sensors measuring at least volume fluctuation of the residual limb, pressure changes inside the prosthetic socket, and relative movement between the residual limb and the prosthetic socket; and
   a control system operably connected to the pump mechanism and the sensors, the control system arranged to receive data from the sensors representative of the pressure changes inside the prosthetic socket, the relative movement between the residual limb and the prosthetic socket, and the volume fluctuation of the residual limb over a period of time, and generate vacuum performance information representative of an effectiveness of the pump mechanism by comparing the pressure change inside the prosthetic socket and relative movement between the residual limb and the prosthetic socket when the volume of the residual limb fluctuates.

2. The system of claim 1, wherein the pump system includes a feedback system arranged to communicate information obtained by the pump system to an end user.

3. The system of claim 1, wherein the control system is arranged to direct the pump mechanism to decrease a vacuum in the prosthetic socket if the activity information generated by the control system indicates a user is in a period of inactivity.

4. The system of claim 1, wherein activity information generated by the control system includes at least one of heartrate information and blood pressure information.

5. The system of claim 1, wherein at least one of the sensors is adapted to detect at least one of location or motion of the pump mechanism.

6. The system of claim 1, wherein at least one of the sensors is adapted to detect at least one of location or motion of a prosthetic foot operatively connected to the prosthetic socket.

7. The system of claim 6, wherein the pump system is secured to the prosthetic foot.

8. The system of claim 6, wherein the pump system is secured to an adaptor system extending between the prosthetic socket and the prosthetic foot.

9. The system of claim 1, wherein the pump system is secured to the prosthetic socket.

10. A vacuum suspension system comprising:
a prosthetic socket adapted for receiving a residual limb;
a pump system secured to the prosthetic socket, the pump system including a pump mechanism in fluid communication with the prosthetic socket, a plurality of sensors associated with at least one of the prosthetic socket and the pump mechanism, the sensors adapted to measure at least pressure changes inside the prosthetic socket, relative movement between the residual limb and the prosthetic socket, and volume fluctuation of the residual limb; and
a control system operably connected to the pump mechanism and the sensors, the control system arranged to receive data from the sensors representative of the pressure changes inside the prosthetic socket, the relative movement between the residual limb and the prosthetic socket, and the volume fluctuation of the residual limb over a period of time, and generate vacuum performance information representative of an effectiveness of the pump mechanism by comparing the pressure change inside the prosthetic socket and relative movement between the residual limb and the prosthetic socket when the volume of the residual limb fluctuate.

11. The system of claim 10, wherein the pump mechanism includes a pump housing and a membrane attached to the pump housing such that a fluid chamber is defined between the membrane and the pump housing.

* * * * *